(12) United States Patent
Fields et al.

(10) Patent No.: US 6,733,537 B1
(45) Date of Patent: May 11, 2004

(54) APPARATUS FOR TISSUE EXPANSION USING PULSATILE MOTION

(75) Inventors: Antony J. Fields, San Francisco, CA (US); Gary B. Greenburg, Millbrae, CA (US); Alexander Kazaks, Mountain View, CA (US); Joshua Korman, Los Altos Hills, CA (US)

(73) Assignee: Reconstructive Technologies, Inc., Mountain View, CA (US)

( * ) Notice: Subject to any disclaimer, the term of this patent is extended or adjusted under 35 U.S.C. 154(b) by 157 days.

(21) Appl. No.: 09/585,630

(22) Filed: Jun. 2, 2000

(51) Int. Cl.[7] ............................ A61F 2/02; A61B 17/08
(52) U.S. Cl. ................................. 623/66; 606/213
(58) Field of Search ..................... 623/8, 11.11, 16.11, 623/66; 607/149; 606/215, 216, 218, 213

(56) References Cited

U.S. PATENT DOCUMENTS

| | | | |
|---|---|---|---|
| 3,862,629 A | * | 1/1975 | Rotta ............... 128/DIG. 10 |
| 4,863,469 A | | 9/1989 | VanBeek et al. |
| 4,955,905 A | * | 9/1990 | Reed ................ 604/97.02 |
| 5,549,640 A | | 8/1996 | Fontenot |
| 5,649,960 A | | 7/1997 | Pavletic |
| 5,746,762 A | | 5/1998 | Bass |
| 5,858,003 A | | 1/1999 | Atala |
| 5,928,265 A | | 7/1999 | Fleischmann |

FOREIGN PATENT DOCUMENTS

EP        0 279 534        8/1988

OTHER PUBLICATIONS

Sung, Shin Wee, *Continuous Versus Intraoperative Expansions in the Pig Model*, Plastic and Reconstructive Surgery, Nov. 1992; 808–814.

* cited by examiner

Primary Examiner—David J. Isabella
(74) Attorney, Agent, or Firm—Cooley Godward LLP

(57) ABSTRACT

An apparatus for increasing the rate of expansion of tissue area and volume, either in vivo or in vitro, which comprises a tissue expansion device suitable for expansion of tissue and a controller connected to the device, wherein the controller causes the device to subject the tissue to stretching forces that alternatively increase and decrease to provide a series of stretch and relax phases during a period of tissue expansion without intervention of an operator.

2 Claims, 8 Drawing Sheets

APPARATUS FOR TISSUE EXPANSION USING PULSATILE MOTION

TECHNICAL FIELD

This invention resides jointly in the fields of surgery and tissue culture and is particularly directed to an apparatus used for the expansion of animal tissue from an original, natural size to a larger size, usually with the intention of using the expanded tissue to replace defective tissue in the body of a living patient.

BACKGROUND

Tissue replacement is an essential component of reconstructive surgery after burns, trauma, tumor excision, and correction of congenital anomalies. For example, there are approximately 1 million burns per year in the U.S. alone, which result in about 100,000 admissions to burn units, about ⅓ of which require skin grafting.

The best possible skin available for grafting would be skin from the same patient taken from a donor site elsewhere on the body (referred to as an autograft). Suitable skin graft donor sites, however, are limited not only by body surface area, but can also be affected by previous graft harvest or trauma. There are times, when donor skin is limited and the amount of skin required for grafting is quite large, that sufficient autografts are not available. Because of the importance of the skin in preventing infection, either the donor skin must be used to cover a larger area than it originally covered or some suitable replacement material must be used. Harvesting of multiple skin grafts from the same donor site is often used, but such harvesting requires weeks to months between procedures for new skin to grow on the donor site. It is also a very traumatic technique, since multiple painful operations must be undertaken.

In a similar manner, other tissues also require replacement after traumatic injury, tumor excision, and other medical situations involving tissue loss. Autografts are preferred for muscle, cartilage, tendon, nerve, and other tissue replacement whenever possible in order to reduce host vs. graft immunity issues. Under appropriate circumstances, donor tissues derived from sources other than the recipient are acceptable for both skin and other tissues, but usually only as temporary replacements. For example, in patients suffering from large burns with limited donor skin sites, cadaver allografts are commonly used for temporary skin coverage, but ultimately such allografts are rejected and a permanent autograft is required. In addition, allografts also pose a risk of infection of the recipient by viruses or other disease-causing organisms present in the donor, such as infection by human immunodeficiency virus or hepatitis virus.

Artificial tissues have been developed in order to avoid the problems associated with allografts. For example, to aid in the grafting of skin on patients with limited donor areas, cultured epithelial cells derived from the patient being treated have been utilized in many grafting applications. In general, the cells are used in the form of a monolayer of epithelial cells grown on a culture medium. Preparation of such cultures requires many weeks or months, and the product is quite difficult to handle because of its fragility, even when multiple epidermal cell layers are used to form a multi-layer skin substitute.

Tissue expansion techniques, which were developed as in vivo techniques, have been used in plastic surgery for over a decade and can be helpful in increasing the area of donor tissue. Skin is not the only tissue that can be and has been expanded, although it is the most common. Other tissues have been expanded in surgical and other in vivo situations. Arteries, peripheral nerves, and skin have all been expanded in human clinical trials. Ureter, small bowel, and bladder have been expanded in animal trials.

The techniques used for in vivo tissue expansion are similar for all tissue types and involve mechanically stretching the tissue while the tissue is still attached to the patient's body. For example, by placing an expander subcutaneously and injecting it with saline, skin can be expanded and its surface area increased. This allows reconstruction with local skin after expansion of an adjacent tissue bed.

Background information in the general field of tissue expansion, including techniques suitable for skin grafting and tissue replacement, is available in the patent and scientific literature. A number of exemplary patents and scientific publications are cited below, both as examples of existing technology and to provide additional basis and support for ancillary technology related to the practice of the present invention:

U.S. Pat. No. 5,882,353 entitled "Mechanical tissue expander"

U.S. Pat. No. 5,858,003 entitled "Systems and methods for promoting tissue growth"

U.S. Pat. No. 5,855,588 entitled "Combination dissector and expander"

U.S. Pat. No. 5,788,627 entitled "Cavemosal extension implants"

U.S. Pat. No. 5,776,159 entitled "Combination dissector and expander"

U.S. Pat. No. 5,630,843 entitled "Double chamber tissue expander"

U.S. Pat. No. 5,618,310 entitled "Tissue, expansion and approximation device"

U.S. Pat. No. 5,549,713 entitled "Method for skin tissue expansion"

U.S. Pat. No. 5,507,775 entitled "Tissue expansion and approximation device"

U.S. Pat. No. 5,476,479 entitled "Handle for endoscopic surgical instruments and jaw structure"

U.S. Pat. No. 5,441,540 entitled "Method and apparatus for skin tissue expansion"

U.S. Pat. No. 5,425,760 entitled "Tissue expander apparatus, and methods of constructing and utilizing same"

U.S. Pat. No. 5,158,571 entitled "Tissue expander and method for expanding tissue"

U.S. Pat. No. 5,092,348 entitled "Textured tissue expander"

U.S. Pat. No. 5,005,591 entitled "Self-inflating tissue expander"

U.S. Pat. No. 4,904,267 entitled "Method and device for fixing a joint prosthesis"

U.S. Pat. No. 4,863,469 entitled "Method and apparatus for expanding nerve tissue"

U.S. Pat. No. 4,828,560 entitled "Spring ring tissue expander"

U.S. Pat. No. 4,800,901 entitled "Balloon-type Tissue expansion device"

U.S. Pat. No. 4,643,733 entitled "Permanent reconstruction implant and method of performing human tissue expansion"

U.S. Pat. No. 4,157,085 entitled "Surgically implantable tissue expanding device and the method of its use"

Argenta, "Controlled tissue expansion in reconstructive tissue," Brit. J. Plas. Surg., 37:520–529 (1984)

Argenta et al., "The Use of Tissue Expansion in Head and Neck Reconstruction," Ann. Plast. Surg., 11:31–37 (1983).

Arons et al., "The surgical applications and implications of cultured human epidermis: A comprehensive review," Surgery, 111:4–11 (1992)

Carney, "Generation of autograft; the state of the art," Burns, 12:231–235 (1986).

Chen, "An animal experiment on short gut lengthening," Chin. Med. J. (Engl.), 110:354–357 (1997).

Gallico, "Biologic Skin Substitutes," Clinics in Plastic Surgery, 17:519–526 (1990)

Greenwald et al., "Full-Thickness Skin Wound Explants in Tissue Cultures: A Mechanical Evaluation of Healing," Plastic and Reconstructive Surgery, 90:289–294 (1992)

Kirsner et al, "The Biology of Skin Grafts," Arch. Dermatol., 129:481–483 (1993)

Liatsikos et al, "Tissue expansion: a promising trend for reconstruction in urology," J. Endourol., 14:93–96 (2000).

Nanchahal and Ward, "New grafts for old? A review of alternatives to autologous skin," Brit. J. Plas. Surg., 45:354–363 (1992)

Satar and Atala, "Progressive dilation for bladder tissue expansion," J. Urol., 162:829–831 (1999).

Stifelman and Hensle, "Ureteral tissue expansion for bladder augmentation: a long term prospective controlled trial in a porcine model, " J. Urol., 160:1826–1829 (1998).

Sung Shin Wee et al., "Continuous versus intraoperational expansion in the pig model," Plastic and Reconstructive Surgery, 90:808–814 (1992)

A particularly useful advance in the field of tissue expansion was initiated by Dr. Joshua Korman, who developed the first process for in vitro skin expansion in the 1990s. The investigations of Dr. Korman resulted in the issuance of two U.S. patents, U.S. Pat. No. 5,686,303, entitled "Method of Growing Vertebrate Skin In Vitro," and U.S. Pat. No. 5,914,264, entitled "Apparatus for Growing Vertebrate Skin In Vitro." The method involves growing complete vertebrate skin in vitro by obtaining a segment of vertebrate skin, positioning the skin segment in an artificial cell-growth medium containing sufficient nutrients to maintain growth of cells of the skin, and subjecting the skin segment to stretching forces while the skin segment is in the medium. Skin produced by the method and an apparatus for carrying out the method were also disclosed in these patents.

Even this improvement, which eliminates much of the pain and discomfort associated with in vivo skin expansion, can itself be improved by increasing the rate of tissue expansion in order to improve the life of the patient who is waiting for tissue expansion to be completed so that a defective tissue can be replaced with the expanded tissue.

In the past, investigations in tissue expansion have demonstrated that use of continuous expansion forces in post operative situations over a period of three days or more is superior to intraoperative tissue expansion, even when the intraoperative procedure involved three three-minute cycles of pressure increase and decrease (i.e., a manual procedure performed by the surgeon during surgery). See, Sung Shin Wee et al, "Continuous versus intraoperative expansion in the pig model," Plastic and Reconstructive Surgery, 90:5, 808–814 (1992). Although "cycling of pressure" is mentioned (along with other factors; p.811) in a section discussing potential additional skin expansion, there is no indication that the rate of expansion would be increased by such cycling. Instead, there is simply an indication that the total volume of expansion did not plateau in the study, so that a greater total volume might be obtained by various techniques.

Accordingly, it remains desirable to develop an apparatus that will improve the rate of tissue expansion. Investigations on rate improvement have continued in the laboratory founded by Dr. Korman, and results of those investigations are the subject of the present patent application.

BRIEF DESCRIPTION OF THE DRAWINGS

Certain aspects of the invention will be better understood by reference to the drawings that form part of the specification, in which functionally equivalent parts of various apparatus have the same identifying numbers throughout, wherein.

SUMMARY OF THE INVENTION

Figure 1:
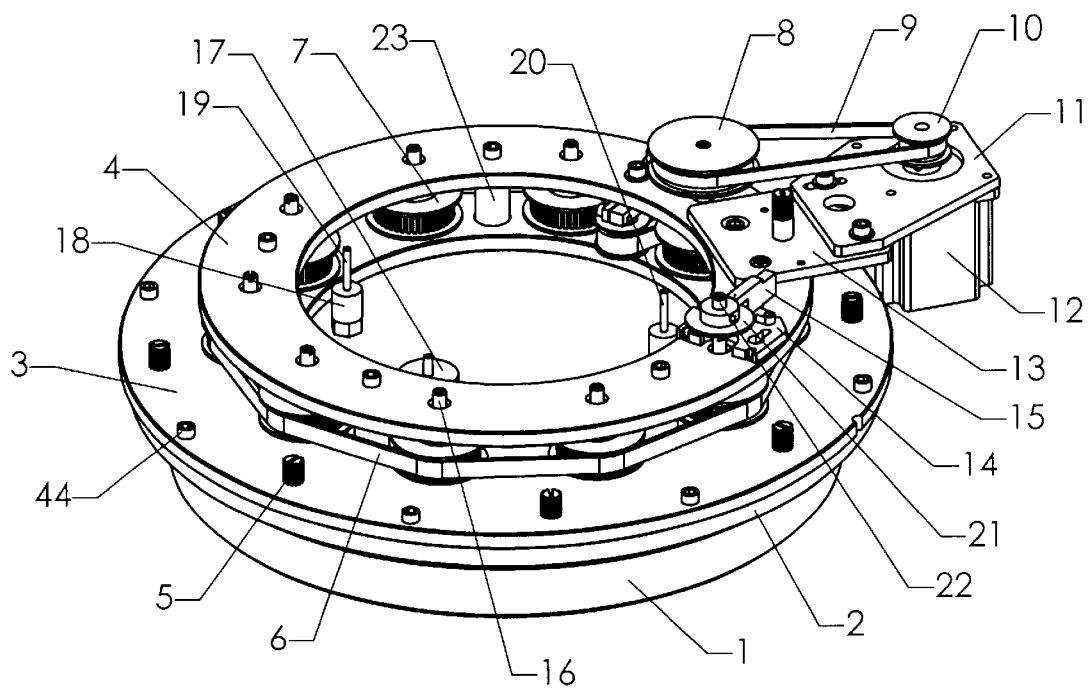
FIG. 1 is a perspective view of a first embodiment of an in vitro apparatus of the invention, shown in final-assembled form. The tissue segment and many working parts that transfer force in the apparatus are not visible in this view, as they are located in the interior of the apparatus.

Accordingly, it is an object of the invention to provide in vivo and in vitro apparatuses useful to increase the rate of tissue expansion. Although skin is the tissue most often expanded, it is an object of the invention described herein to apply the apparatus to all types of living tissue.

Preferably it is an object of the invention to provide an easily cleanable and sterilizable in vitro apparatus that is readily portable between workstations and that allows easy automatic control of stretch and relax cycles.

These and other objects of the invention have been accomplished by providing an apparatus for increasing the rate of expansion of tissue area and volume, either in vivo or in vitro, which comprises a tissue expansion device suitable for expansion of tissue and a controller connected to the device, wherein the controller causes the device to subject the tissue to stretching forces that alternatively increase and decrease to provide a series of stretch and relax phases during a period of tissue expansion without intervention of an operator. The increases and decreases in stretching forces are referred to as being positively modified in order to distinguish them from naturally occurring changes that may occur, for example, when movement of the body (in an in vivo expansion) causes an increase in the pressure exerted by a subcutaneous fluid expander or when stretching forces decrease naturally as tissue growth occurs (for either in vivo or in vitro expansion). Although the positively controlled increase and decrease in stretching forces can occur at any of a variety of cycle rates, manners, and durations (e.g., sinusoidal increase and decrease or rapid expansion followed by rapid force reduction), minimally there is at least one cycle per day for a period of at least one day. The expanded tissue is available for use in reconstructive surgery (or any other purpose) as soon as it has expanded to the desired size. Experimental evidence has shown that the growth in tissue size is more rapid relative to similar methods that operate without alternatively and positively increasing and decreasing the stretching forces.

In various embodiments of the invention, the stretching forces are orthogonal or radial relative to each other, but they can also be of different geometry, such as linear stretching of elongated tissues such as ligament or nerve tissue. The tissue is preferably human for use in human recipients, but veterinary use of the new skin is also encompassed by the invention. Other embodiments of the invention are set forth below in detail.

DESCRIPTION OF SPECIFIC EMBODIMENTS

The present invention relates to an apparatus that combines a number of previously known techniques in a novel manner to achieve results not previously obtained. Namely, by alternatively and positively increasing and decreasing the stretching forces applied to tissue in vitro during tissue culture or in vivo while still attached to a living body, size of the tissue can be increased more rapidly than was previously achieved using constant pressure. The reason for this increased growth rate is not known, but it is believed to be at least in part the result of providing a rest phase for tissue growth after the stress of a stretching force that realigns and/or breaks down collagen and/or other structural components of tissues.

There are a number of technologies ancillary to the present invention that are well developed and that thus will not be described here in great detail, such as methods for excision of the original skin or other tissue segment, production of culture media for the growth and maintenance of intact tissue when an in vitro method is used, and grafting techniques for the attachment of the graft to the host. Such methods and materials are exemplified here and references are given to scientific publications, where appropriate, so that the invention can readily be practiced. It will be recognized, however, by one of ordinary skill in the art, that many variations of these ancillary methods and materials exist and that the invention is not limited to the specific examples provided here.

In general, the apparatus will be used with a method that calls for enlarging tissue taken from a donor site of an animal donor (which includes humans). Details of the method are described in a concurrently filed application from the laboratories of the present inventors entitled "Method for Tissue Expansion using Pulsatile Motion" and identified by attorney docket number RECT002/00US, which is herein incorporated by reference.

The apparatus of the invention consists of two parts, one part being referred as a "tissue expander" and the other being referred to as a "controller." Here the term "tissue expander" (also sometimes referred to herein as a "tissue expansion device suitable for expansion of tissue") is used more broadly than these same words are normally use in the field of reconstructive plastic surgery. In that field, "tissue expander" has been used to refer to balloon-type devices intended for insertion under the skin and used for in vivo expansion of tissue, usually skin. In this specification, "tissue expander" and its equivalent terms refer not only to such balloon-like devices implanted under skin and used in vivo but also to all other mechanical devices that actually supply the mechanical stretching force to the tissue, whether in vivo or in vitro.

Many of existing tissue expanders (including the ones described in the prior art discussed above) can be converted into an apparatus of the invention by addition of a "controller." Here "controller" refers to the part of the overall device that causes the device to subject tissue to stretching forces that alternatively increase and decrease so as to provide a series of stretch and relax phases during a period of tissue expansion without intervention of an operator. The controller can be integral with or separate from the mechanical, force-applying portion of the apparatus and can be mechanical (e.g., a mechanical arrangement of gears, levers, drive belts, or other moving parts connected to the power sub-component, such as are typically found in clocks and other mechanical devices that keep time) or electronic (e.g., a computer or other computational device programmed to send and receive signals at appropriate times). In either case where the controller is provided as a separate component, a controller connection (such as belt drive for the mechanical case or a cable connection for the electronic case) can be present as part of the mechanical apparatus so that the mechanical apparatus can be connected to and exchange information with the controller.

The mechanical sub-components of an apparatus in which in vitro tissue culture and stretching takes place can vary widely, being either simple or complex. An example of a simple apparatus is a Petri (or similar) dish containing a tissue-culture medium and having a set of clamps, wires, pulleys, and weights arranged so that the clamps can be attached to a tissue segment in the medium and subjected to alternatively increased and decreased forces applied to clamps by weights attached to the clamps by the wires and suspended by the pulleys to reduce friction. The controller in this case causes weights to be changed on a schedule to provide the required variation in force. A more elegant apparatus could contain electric motors for supplying alternating levels of force to the clamps or for circulating the culture medium in the apparatus, sensors to measure forces and stretching distances, reservoirs for fresh and waste medium, controlled atmospheres, and the like. Minimally, the mechanical parts of an apparatus of the invention intended for in vitro use will comprise a container for holding a tissue culture medium, at least two tissue connectors for holding a detached tissue segment in the culture medium, and a component that supplies opposing forces via the connectors to the tissue segment (sometimes referred to as the power sub-component). As noted above, a controller that allows for automatic application of a series of stretch and relax cycles can be either an integral part of the mechanical apparatus or can be a physically separate sub-component. The container for the tissue medium can also be an integral part of the apparatus or can be a separate container that is retained by the apparatus at a specific location so that moving parts associated with stretch and relax cycles fit into the medium container at appropriate locations. In the later case the tissue connectors are "in" the container by being affixed to the parts of the apparatus that will engage the container.

An alternative in vitro apparatus can comprise a tubular fluid reservoir having an open end, a clamp located at the open end of the reservoir, where the clamp is adapted to seal the skin segment over the open end to provide a fluid-tight seal, means for supplying hydrostatic pressure to a fluid located in the reservoir, and a controller that allows for automatic application of a series of stretch and relax cycles. It should be recognized here that "tubular" does not require a circular cross section, as the word is used here. Examples of means for supplying hydrostatic pressure comprises (1) a nutrient reservoir fluidly connected to the tubular fluid reservoir and being located at a higher gravitational potential than the skin segment when the apparatus is located in its normal operating position or (2) a pump fluidly connected to the tubular reservoir. A pump is any mechanical device that moves fluid from one location to another and includes a hydraulic piston. An example of a suitable clamp would be an annular member adapted to fit tightly against a flange on the open end of the tubular reservoir, with holes or grooves in the flange or annular member (or both) adapted to contain screws, bolts, wing nuts, or the like for fastening the annular member against the flange, with the skin segment being located between them to provide a fluid-tight seal at the end of the tubular reservoir with the skin being attached over the end of the reservoir as in a drum. Since freshly harvested skin is resilient (as are many other planar tissues, such as mucosal linings), no additional seal is required, but a flexible sealing member (such as an O-ring) can be provided between, e.g., the flange and annular member, if desired. Changes in the desired forces can be provided by moving the reservoir up and down relative to the tissue or by changing the pressure supplied by the pump.

In a similar manner, both simple and complex in vivo tissue expanders can be prepared. Such apparatuses typically comprise an expandable balloon-like structure that is implanted subcutaneously in the patent. Access ports are provided so that fluid can be injected into the balloon, causing it to expand and exert the stretching forces. Simple devices consist entirely of the balloon-like expander and a septum through which fluid can be manually injected through the skin via a syringe, along with the necessary controller (or controller connection). More complex devices have percutaneous catheters leading to external pumps and pressure controllers, specific geometries intended for expansion of different tissue (or different locations of the same tissue, e.g., different skin areas), and other apparatus components.

One example of these more complex in vivo apparatuses that include pressure controllers is provided in U.S. Pat. No. 4,955,905. This patent discloses a pressure monitor for use in connection with tissue expander envelopes implanted beneath the tissue of the skin wherein a liquid is injected into the envelope to cause expansion of the skin or tissue and additional liquid is periodically injected to cause progressively increased expansion of the tissue. The tissue monitor includes means establishing direct communication between the pressure monitor and the liquid injected under pressure whereby the monitor will provide a reading of the internal liquid pressure in the envelope. The method described in this patent comprises the steps of implanting an inflatable envelope beneath the skin, injecting a sterile solution under pressure through a fill line communicating with the envelope, interrupting the flow of liquid under pressure into the envelope, sensing the pressure level of liquid injected into the envelope, and adjusting the pressure level when necessary either by removing from or injecting liquid into the envelope.

This last operation superficially resembles the method of the present invention, but differs in that there is no positive cycling of pressure, simply a monitoring of pressure, followed by an immediate adjustment if the envelope has been filled with too much liquid. According, the apparatus is different in that it does not contain a mechanism (whether mechanical or electronic, via controls) that will cause the automatic application and release of stretching forces that is required of an apparatus of this invention.

A key aspect of an apparatus of the present invention is that the controller portion of the apparatus automatically (without human intervention after set up) subjects a tissue to stretching forces that are controlled so that the tissue experiences a "stretch and relax" cycle. Here "stretching forces" means a force or forces applied to the tissue in one or more direction in which expansion (i.e., tissue growth) is desired. Because of the physical nature of stretching forces, at least two opposed forces are applied to a tissue (because of Newton's familiar law of equal and opposite forces). If only two opposed forces are present the stretching is along a line coaxial with the stretching forces, subject to some additional stretching along adjacent regions of the tissue. This is the simplest stretching situation, but is not particularly desired (other than for substantially linear tissues, such as nerve, tendon, and ligament tissue) because of the resulting tissue deformation. Additional forces can be applied to provide for more regular stretching of volumetric or planar tissues, such as muscle or skin. Parallel opposed forces (such as would be applied by two broad, rigid clamps attached to opposite ends of a detached skin segment) lead to stretching along a single dimension of a tissue. Non-parallel multiple stretching forces (e.g., radial outward from a central point or orthogonally in the plane of a tissue) result in stretching in both of the two dimensions of a planar tissue (e.g., the two dimensions parallel to the plane of a skin surface). Forces can be supplied in three dimensions as well.

Forces can be applied to planar tissues, such as skin, that are not entirely parallel to the skin surface. However, some portion of the force must be parallel to the planar surface for stretching to take place. For example, when used with in vitro stretching of skin, a convex solid surface or a fluid forced against the face of a detached skin segment whose edges are fixed will cause the skin segment to be subjected to forces both orthogonal and parallel to the surface of the skin; such stretching comes within the scope of the present invention. This is the type of stretching of skin that occurs with the fluid-expandable balloons and envelopes that are common in in vivo skin expansion.

When a detached tissue segment is being stretched in an in vitro application, the ends of the segment are held in place in the tissue culture by some physical apparatus. Any apparatus that can be used to hold the ends in place can be used. An attachment apparatus is needed for each point to which a force will be applied. Typical attachment apparatuses include clamps, hooks, sutures, and glue. A clamp can be narrow (e.g., less than ¹/₁₀ the length of the edge being held) or broad (up to or greater than the width of the edge, and generally considered broad when greater in width than ½ the width of the edge of the tissue being clamped). If opposed broad clamps are used, stretching between the ends of the clamp will generally be restricted if an orthogonal stretching force is also present on the skin. For maximum stretching efficiency, multiple attachment points capable of moving away from each other during the stretching process are preferred. For example, multiple small hooks or clamps attached in a generally circular manner to a circular detached skin segment and subjected to forces applied radially outward from the center of the segment automatically move away from each other as stretching proceeds, thus supplying stretching forces along the tangents of the circle as well as along its radii.

The forces themselves can be supplied by any subcomponent capable of supplying force, such as a weight, spring, or motor. The force being applied at any given point of the cycle can be either static or dynamic. Here a static force is one that is applied between two attachment points that do not move further apart from each other as cell growth and division occurs. Such growth reduces over time the force between the attachment points. For example, two clamps can be attached to opposite ends of a detached skin segment, with one (or both) of the clamps being attached to a screw so that the distance between the clamps can be varied. Turning the screw to move the clamped ends away from each other produces an initial force on the skin segment, but this force decreases as cells in the skin grow and divide. A dynamic force, on the other hand, is one provided between two attachment points that are capable of relative movement so that a constant force can be maintained. For example, two clamps can be attached to weights that are suspended via a pulley system from opposite ends of a detached skin segment. The force on the skin segment in such an apparatus remains constant as the skin grows and divides.

The amount of force applied at any given point in time to a tissue during a stretch phase is minimally that required to cause the tissue to stretch and will not exceed the amount that causes the tissue to rupture. Since the strength of different tissues obtained vary (even tissues obtained from different locations of the same donor/recipient of an autograft), the forces are best determined empirically. Minimum stretch-cycle force is that which causes some stretch to take place. Maximum stretch-cycle force is that which causes tissue necrosis. Preferably, maximum force is less (typically at least 5% less) than that which causes blanching of tissue as a result of the inability of the tissue to maintain blood flow through internal blood vessels. In in vivo situations, patient pain will also be significant in determining maximum forces that can be used.

For example, with the use of human skin, stretching of at least 2% per day is desired, preferably at least 5%, more preferably at least 10%. Non-human skin can be either tougher or less tough (here "tough" refers to resistance to stretching) than human skin and thus may be stretched correspondingly less or more than these amounts. In general skin can be stretched until rupture or cell death induced by the tension of stretching, which can readily be followed by histological examination. In some cases it may be desirable to keep stretching under 15% per day to avoid cell death, in other cases under 12%. However, the maximum sustainable stretch rate is best determined empirically, using these numbers as initial guidelines. When skin is initially placed in the nutrient medium, it should be stretched back to original in vivo size before actual stretching is measured, since skin removed from a body generally shrinks to less than its original dimensions.

In many cases, the actual forces will never be measured or known, such as in a screw-based apparatus. However, typical forces for skin range from zero to 300 g per attachment point, preferable zero to 150 g per attachment point, using one attachment point per cm of skin perimeter. As there is variation from patient to patient in strength of skin and other tissues, one should start with a force at the lower end of the range and increase forces gradually during the initial stretch, paying attention to counter indications, such as cracking or tearing of the tissue. Instead of calculating on a per attachment basis, force can be measured per unit area. This is particularly useful for skin, as area of coverage is often the matter of primary interest. For example, skin in the form of a disk 2.93 cm in diameter, having an area of 6.75 cm$^2$, preferably has an applied force of 75–225 g/cm$^2$, more preferably 150 g/cm$^2$. On a per attachment scale, this translates to a range of 50–200 g/attachment, preferably 100 g/attachment.

Positive control of the stretch and relax cycles is an important part of the present invention. The "stretch" phase of a cycle occurs while stretching forces are increasing or are being maintained at a level that causes stretching to occur. The "relax" phase of the cycle occurs when stretching forces are decreasing or are being maintained at a level less than the maximum used during the preceding "stretch" phase. Gradual reduction of stretching forces as stretching occurs in a static tension device is not considered to provide a relax phase, as a relax phase requires that stretching forces be reduced faster than that which occurs in this static situation. Stretching forces on the tissue can fall to zero during the relax phase, but also can be maintained at a fraction of the force applied during the stretch phase, such as one-half, one-third, or one-quarter of the maximum stretch force.

Because a goal of the present invention is to maximize the rate of tissue expansion, the stretch phase will typically apply the maximum stretching forces that can be sustained without harm to the tissue for the stretch period being used. Relatively higher forces have been found to be acceptable for tissue when applied for shorter periods, while longer stretch cycles are expected to have better success when less than the maximum stretching force is applied.

Forces during the relax phase may not be zero but can be maintained at some positive value in order to maintain some minimal stretching force on the tissue as it recovers from the stretch phase. Typically, the relax phase will have a minimum force that falls in the range of from zero to 0.9 (preferably zero to 0.5, more preferably zero to 0.3, even more preferably zero to 0.1) times that of the maximum stretch-phase force. Most preferably the relax phase minimum will occur with no force being applied to the tissue being expanded.

In order for the present invention to be practiced, stretch and relax periods must alternate. The precise manner in which they alternate, however, is less important. For example, an automated apparatus (used either in vivo or in vitro) can cycle through a series of stretch and relax periods in a simple "on/off" mode (i.e., a graph of pressure versus time would appear as a square wave). Force can also increase (and later decrease) through a series of steps separated by periods of constant force, rather than through a single increase in force. On the other hand, use of two expandable reservoirs, with fluid being pumped back and forth between the two, would produce a sinusoidal graph of stretching forces at the two locations (with each location being out of phase relative to the other; i.e., one location would be in a rest phase while the other is in a stretch phase). Other techniques (such as raising and lowering of a fluid reservoir connected to a single expander) will also produces sinusoidal force/time effects.

Successive cycles can have the same maximum and minimum pressures if desired, although this is not required. Because tissue expansion occurs slowly over time, a typical pattern of pressure cycles will result in slightly lower pressures being exerted with each cycle as stretching occurs and relieves the pressure, unless the expander is adjusted for the new resistance of the skin or other tissue being expanded. For example, in the on/off and two-reservoir systems just mentioned, each cycle will produce slightly lower pressure at the expansion sites unless additional fluid is added to the system (or greater motion of a stretching arm occurs) to make up for the volume added from tissue expansion. However, one can use dynamic forces or can use force applicators (e.g., motors) with feedback control in order to provide the same force (or a pattern of increase and/or decrease in maximum and/or minimum force) in successive cycles, if desired.

The time period of one stretch/relax cycle can vary considerably. One cycle per day (approximately) is the minimum needed to see an increase in expansion rate relative to static application of stretching forces or relative to use of an initial static stretching force or pressure followed by a slow decrease in forces as tissue expansion occurs. Rapid cycling is also possible and appears to improve the expansion rate, perhaps because of an improvement in the circulation of blood or other nutrients through tissue. There is no specific maximum cycle rate, but approximately 100 times per minute is a useful practical limit for many tissues in order to avoid the dangers associated with rapid movement and the possibility of tissue tears or ruptures. More typical cycle rates are from 1 cycle per 10 minutes to 50 cycles per minute, preferably from 1 to 25 cycles per minute, and more preferably from 5 to 15 cycles per minute.

It is not necessary that the stretch and relax phases have the same length, nor need they occur continuously. For example, a series of relatively rapid stretch and relax cycles (an "active" stage) can be followed by a relatively long relax phase (an "off" stage) to allow tissue recovery and growth. A typical example of this technique (illustrated with an operating cycle frequency of 10 stretch and relax cycles per minute) would have an active stage lasting 18 seconds (3 cycles) followed by an off stage lasting 42 seconds (7 "cycles").

The duration of the tissue expansion process will vary with the health and condition of the donor tissue, the extent of expansion necessary for the particular donor tissue being expanded, the health of the patient/recipient of the tissue, and on many other medical factors that are outside the scope of this invention. One day (24 hours) can be considered to be the lower limit of the time during which tissue expansion with pulsatile motion is likely to be practiced, from a practical point of view. Shorter periods of time do not provide sufficient expansion to require the greater complexity of the invention, relative to standard techniques of tissue expansion. There is also no limit on maximum duration, other than patient discomfort in in vivo situations and tissue viability during tissue culture. The advantages of the method of the invention relative to non-pulsatile techniques will be more apparent as the duration of treatment increases, so that minimum expansions of two days or more are preferred.

These examples of cycles, including factors such as force/time relationships, relative forces, duration of the process, and the like, should not be considered to be limiting, as many other force/time waveforms will give satisfactory results of increased expansion rate relative to that which is obtained in the absence of alternating stretch/relax cycles.

A typical expanded tissue has an area or volume after being subjected to stretching forces (over an appropriate length of time) that is at least twice that of the tissue prior to being subjected to the stretching forces. The stretched tissue can be used as a graft or (in in vitro situations) can be divided into further segments so that one or more of the further segments is subjected again to the method of the invention. As long as cell growth continues, new normal tissue can be produced from parts of the original donor graft. For example, skin having a surface area at least two times that of the original donated skin segment can be provided in one stretching operation (which may last over several days), usually at least four times, and often at least eight that of the original. Since the stretched tissue can be divided and the resulting segments re-stretched, exponential production of skin and other tissue is possible, particularly in in vitro situations.

Once a stretched skin graft product has been prepared, it is used in skin grafting in the same manner as an unstretched graft donor skin segment.

Figure 5:
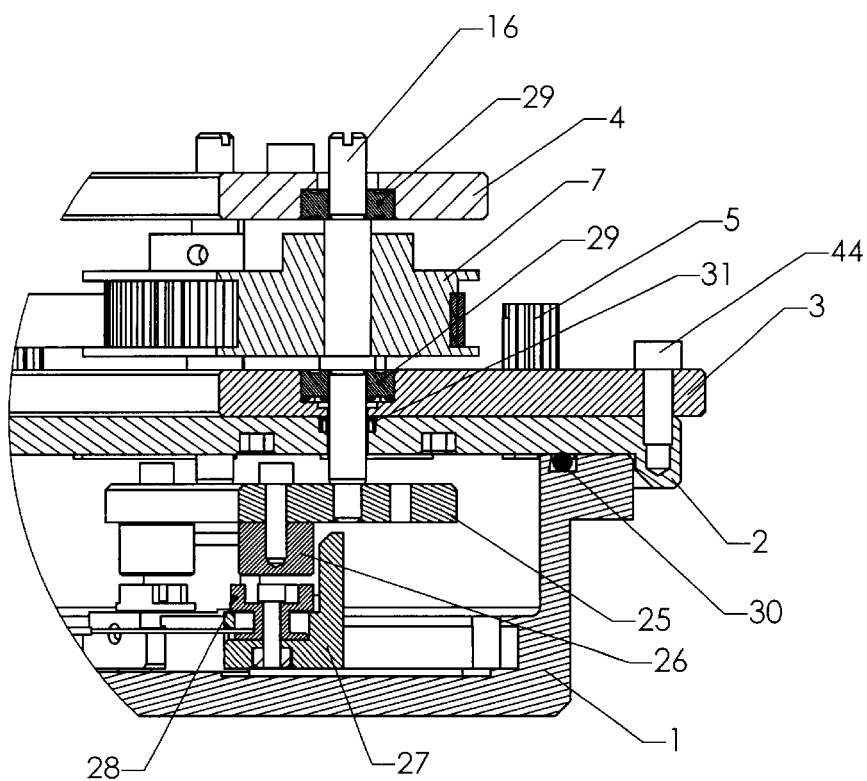
FIG. 5 is an expanded vertical cross-sectional view of the area indicated by circular area 5 as shown in FIG. 4.

Turning now to a specific embodiment of an apparatus of the invention, FIG. 1 shows a perspective view of an in vitro apparatus that embodies the principle of automatic tissue expansion described above. Tray 1 holds a medium used to keep the tissue alive and vital during expansion and to serve as a base for the remainder of the apparatus. Lid 2 sits atop tray 1 and serves both to protect the tissue and medium from contamination and as a support for attachment of various actively moving components described below. A lower bearing support plate 3 rests on top of lid 2, to which it is attached by connector 5, shown in this embodiment as a thumb screw. In this embodiment, lower bearing plate 3 is separate from lid 2 to permit use of a lip seal 31 trapped between plate 3 and lid 2 and around the shafts 16 of synchronization pulleys 7 at the points where they enter the interior of the apparatus. Details of this seal (seal 31) are shown in FIG. 5. Other embodiments of the apparatus can provide this seal in a different manner, in which case plate 3 and lid 2 can be combined into a single lid/plate. Plate 3 and lid 2 are held together by a series of screws 44 as shown here and in FIG. 5. Connectors 5 allow the user to clamp the lid shut by attaching to tray 1 through plate 3 and lid 2 (also shown more clearly in FIG. 5). This ensures that the medium does not spill during movement of the apparatus and that the medium remains sterile, which makes the apparatus conveniently portable.

A series of synchronization pulleys 7 are located near the outer edge of the top face of lid 2, evenly spaced in this embodiment, with the lower end (not visible in this view; see FIG. 5) of the pulley drive shaft 16 inserted into lower bearing plate 3. An upper bearing support plate 4 provides support for the upper end of pulley drive shaft 16, so that the synchronization pulleys 7 are supported in a vertical position on top of tray 1 and lid 2. Support posts 23 maintain upper and lower bearing support plates 4 and 3 firmly in their proper relative positions.

A main drive timing belt 6 engages all pulleys 7 so that all pulleys rotate at the same time. Preferably, the cams (see below) that engage the tower end of individual drive shafts 16 are adjusted so that they reach the maximum stretch and relax positions at the same time. However, simple rotation of individual synchronization pulleys 7 prior to their being linked by timing belt 6 allows for more complex stretching by allowing individual pulleys (and thus individual stretching motions) to be in or out of phase at the choice of the user.

Motion of the pulleys 7 is controlled by step motor 12, which is attached to upper bearing support plate 4 via motor adjustment plate 11 and motor mount plate 13. Motor pulley 10 engages motor drive timing belt 9, which in turn engages drive pulley 8. Motor drive timing belt 9 is properly tensioned by moving motor adjusting plate 11 relative to motor mount plate 13 and locking it in place (shown in this embodiment by the action of locking screws). Drive pulley 8 is attached to the upper end of an extended pulley shaft 22 of one of the synchronization pulleys 7, thus allowing rotation of step motor 12 to be transmitted to that synchronization pulley (and by connection through main drive timing belt 6 to the other synchronization pulleys), and thus to the tissue undergoing expansion, as described below in detail.

Motion of the various supports attached to the tissue (and thus the stretching forces on the tissue) is controlled in part in this embodiment via an infrared interrupter sensor 15 that detects the position of rotating flag 21 attached to extended shaft 22 at one of the synchronization pulley locations. Sensor 15 is properly located on upper bearing support plate 4 via sensor mount 14. Signals are sent by sensor 15 to a controller (often a stand-alone laboratory computer programmed to send and receive various control signals; not shown in this embodiment). The controller provides appropriate signals to step motor 12 so that forces are applied to the tissue being expanded in the desired manner. As noted in the previous description of operation, such motion can either be continuous or in a series of discontinuous steps. Step motor 12 can be operated in either direction and stopped prior to a complete rotation, which allows for partial rotation of the stretching cams. This allows the embodiment as shown to operate with different size tissues and to provide a variety of operating forces without adjustment of the mechanical components, simply by changing the amount that step motor 12 rotates under control of the controller.

Fresh tissue media can be supplied to the tissue in tray 1 via a series of fluid supply ports, located in this embodiment in lid 2. Media supply tube 20 provides access of fresh media to the interior of tray 1, while media return tube 19 withdraws spent media. The height of media return tube 19 in tray 1 can be adjust by sliding tube 19 up or down through compression fitting 18. This determines the fluid level in the device. For example, when skin is being stretched, the medium level can be adjusted to just below the epidermis of the tissue.

Fluid level is maintained by pumping media out of the device at a rate that is faster than the rate at which media is being pumped into the device. This, by necessity, means that air is drawn into the return line. Filter 17 is provided in the air inlet to ensure sterility of the incoming gases. The two-rate pumping process thus also automatically introduces fresh gases (e.g., air or oxygen, optionally supplemented with carbon dioxide) into the space above the medium located in the interior of tray 1.

Figure 2:
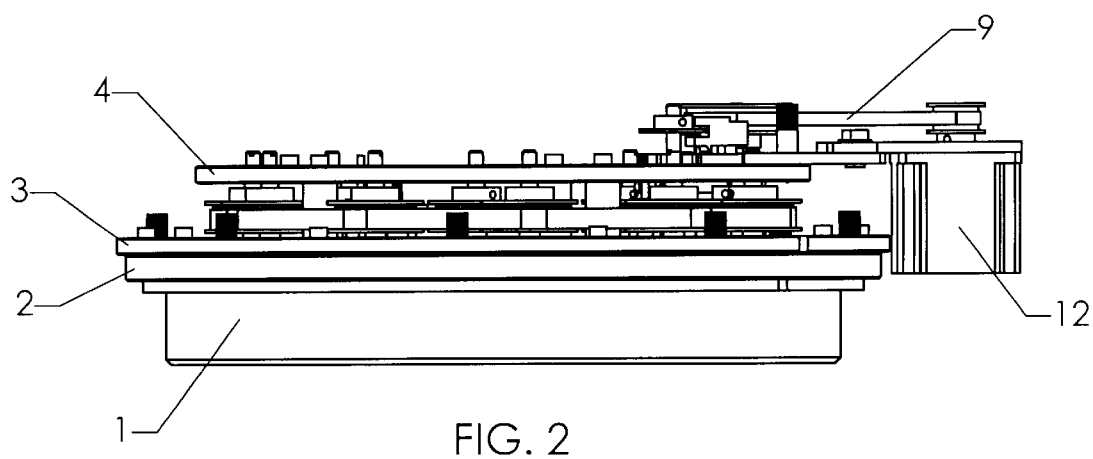
FIG. 2 is a vertical planar view of the embodiment of FIG. 1.

FIG. 2 is a side planar view of the same embodiment shown in FIG. 1 and provides a better view of the stacked relationship of the four main structural elements, namely tray 1, lid 2, lower bearing support plate 3, and upper bearing support plate 4.

Figure 3:
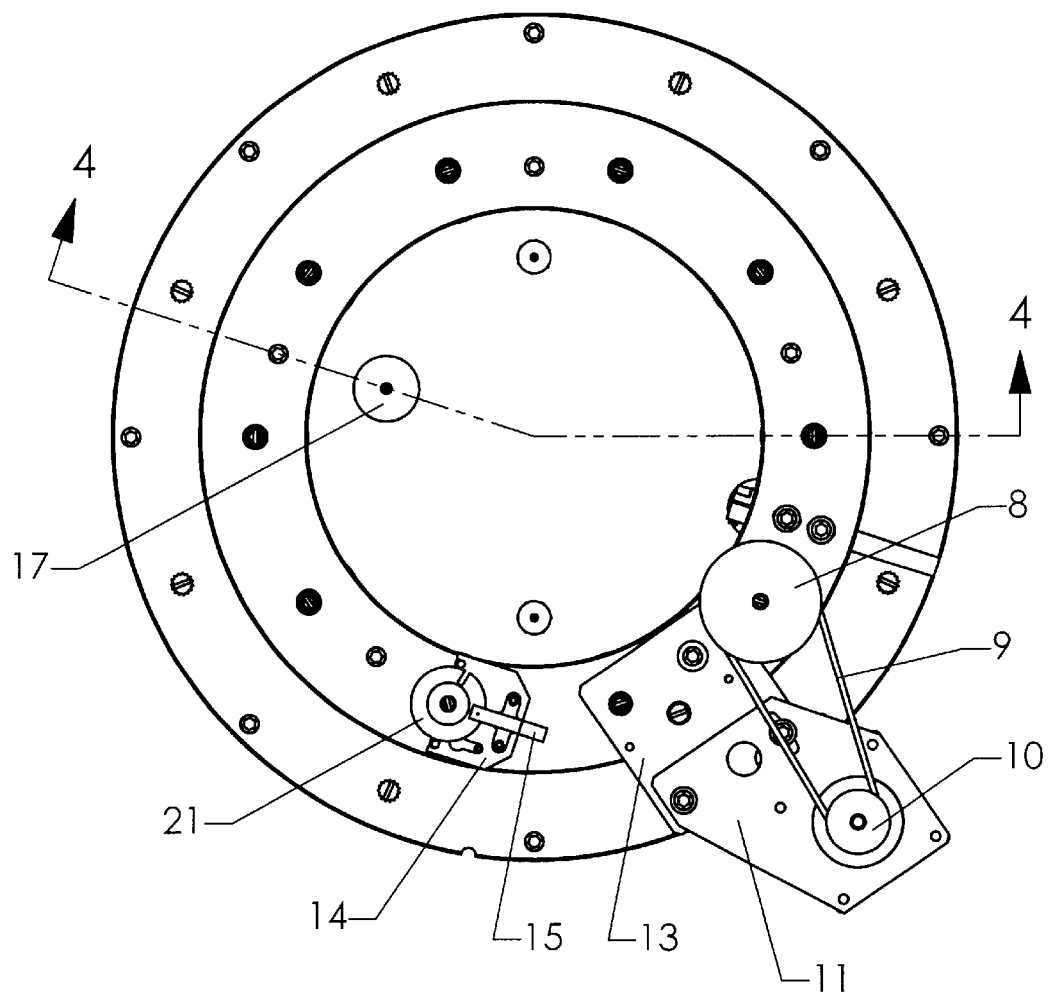
FIG. 3 is horizontal planar view of the embodiment of FIG. 1.

FIG. 3 is a top planar view of the embodiment of FIG. 1, showing the relationship of drive elements to each other, including drive pulley 8, motor drive timing belt 9, motor pulley 10, motor adjusting plate 11, and motor mount plate 13. This view also more clearly shows operation of sensor 15, which is located on sensor plate 14 so that rotation of flag 21 results in a slot in the flag passing in front of the detector portion of the sensor, which typically comprises an infrared source on one side of the rotating flag and a detector on the opposite side. In this manner, the relative position of the underlying cam (and thus the stretching force being applied at a given time) can be detected from the relative position of the synchronization pulley to which flag 21 is attached.

Figure 4:
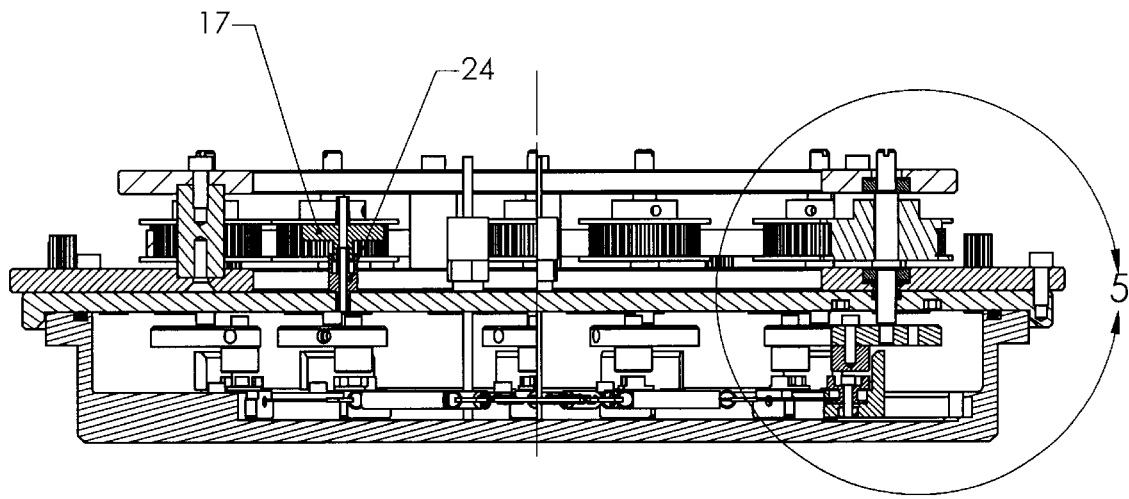
FIG. 4 is a vertical cross-sectional view of the embodiment of FIG. 1, which shows a tissue sample and tension springs, along with associated connectors, in place in the media tray.

FIG. 3 also shows the location of the cross-sectional view given in FIG. 4, as indicated by the broken line and arrows. The two sides of the cross-section view shown in FIG. 4 are at a slight angle to each other to provide a single view with details of different interior parts within tray 1 and other parts of the apparatus.

Attention is directed first to the left portion of FIG. 4. As shown here, filter 17 fits into lid 2 via a Luer fitting 14, which allows easy replacement of the filter then the apparatus is cleaned and sterilized between uses. The cross-sectional view in the right portion of FIG. 4 passes directly through a synchronization pulley 7 and shows previously hidden details of the engagement of the lower portion of the pulley apparatus with the cam that transmits force to the tissue being expanded. Because of the presence of a number of inter-related components in this part of the apparatus, an expanded section, indicated by the circled region, is shown in FIG. 5.

FIG. 5 is a cross-sectional expanded view showing how force is transmitted from step motor 12 (not seen in this view) to the tissue sample. The principal structural elements, tray 1, lid 2, lower bearing support plate 3, and upper bearing support plate 4, provide for containment of the medium and attachment of the other working elements. An O-ring 30 ensures that the interior of tray 1 is sealed when the connectors in lid 2 are engaged.

Shaft 16 of synchronization pulley 7 passes through lower bearing support plate 3 and upper bearing support plate 4. The shaft is guided in rotation by two ball bearings 29, one in each of the bearing support plates. A lip seal 31 is present at the point where shaft 16 passes through lid 2 and is trapped between lower bearing plate 3 and lid 2 when they are in contact in order to maintain sterility of the medium in the interior of tray 1. This seal is preferably made of polytetrafluoroethylene, both for smoothness and durability during sterilization of the apparatus.

The bottom end of shaft 16 axially engages a cam plate 25, which has a cam pin 26 attached to its perimeter (other shapes and attachments of cams are possible in other embodiments). Cam pin 26 is positioned so that it engages sliding tensioner 27. Rotation of shaft 16 thus is transmitted to sliding tensor 27. Initial operating tension on the sample is set by a tension adjusting pulley 28, whose operation is described in more detail in later figures.

Figure 6:
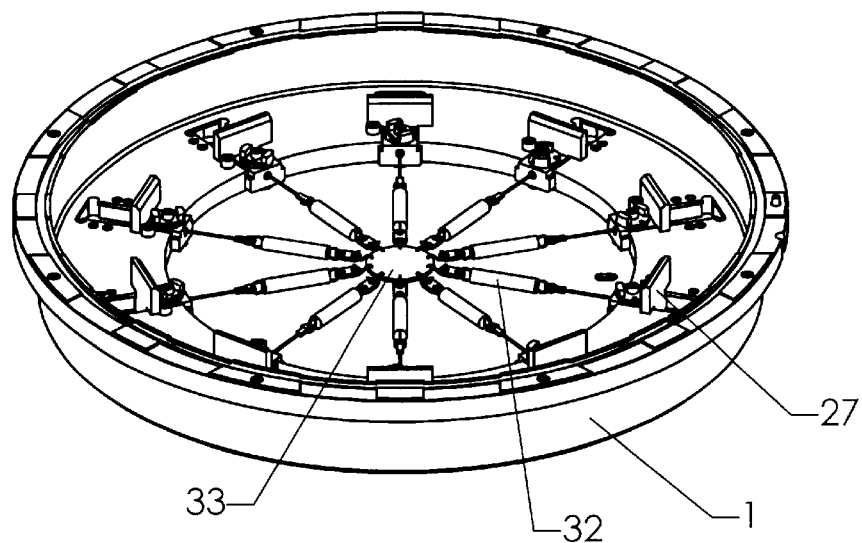
FIG. 6 is a perspective view of the media tray of the embodiment of FIG. 1, shown without the lid (and other parts attached above the tray) in order to show a tissue segment and the tension springs and other connectors used to link the tissue segment to the remainder of the apparatus.
Figure 7:
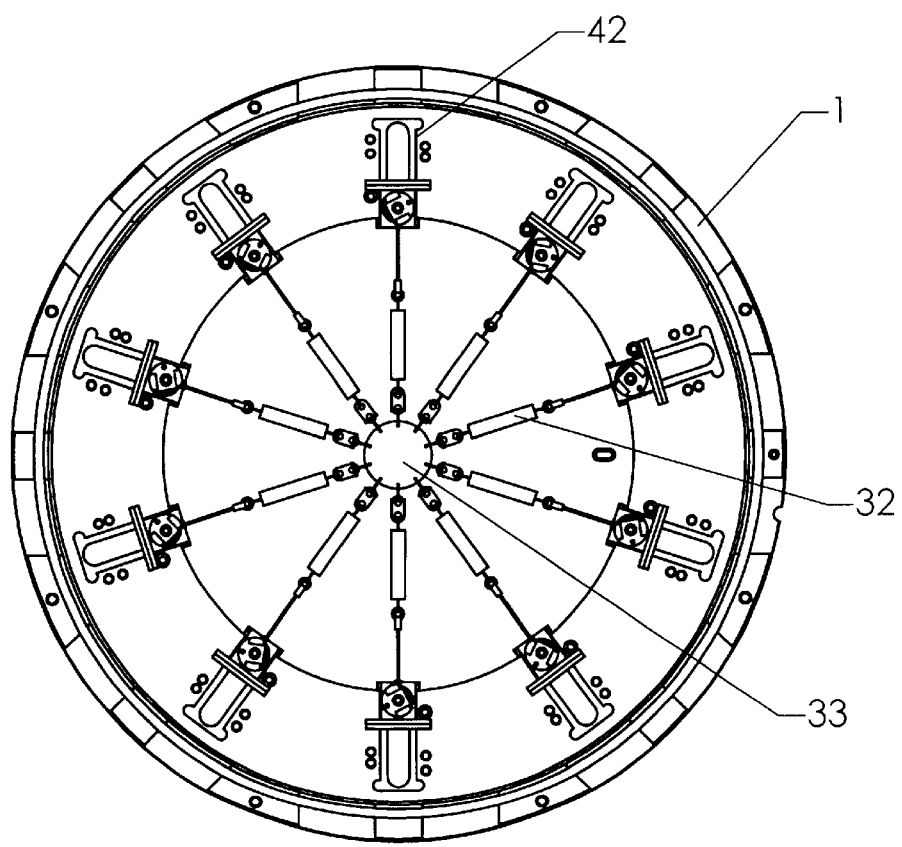
FIG. 7 is a horizontal planar view of the embodiment of FIG. 6.

Operation of sliding tensioner 27 to apply force to a sample when cam pin 26 is rotated is better understood by reference to FIGS. 6 and 7, which show perspective and top planar views of tray 1 containing a tissue sample 33 and having lid 2 removed so that the interior of tray 1 is visible.

A series of sliding tensioners 27 are seen located in their sliding mounts 42, visible at locations around the perimeter of the bottom of tray 1. Tissue 33 is attached via an extension spring 32 and other connectors (described later) to each of the sliding tensioners 27. Each extension spring 32 pulls the corresponding sliding tensor 27 in an inward direction when the tensioner is at the outer range of motion in its sliding mount 42 (the stretch phase of operation). When at the inner range of its motion, no force or a lesser force is transmitted to the tissue (the relax phase of operation). As synchronization pulleys 7 (not visible in this view) rotate and cause cam pins 26 to engage sliding tensors 27, stretch and relax phases occur as tension on the sample increases and decreases.

Figure 8:
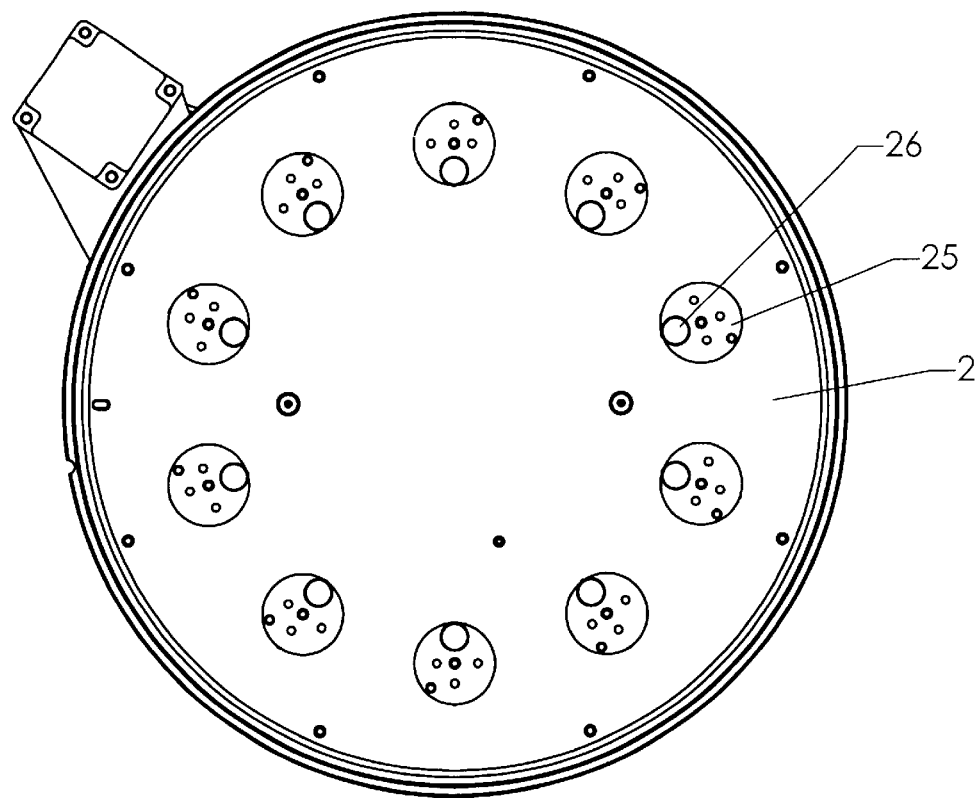
FIG. 8 is a planar view of the lid of the embodiment of FIG. 1 from below, showing the placement of cam pins and plates on the lower lid surface.
Figure 9:
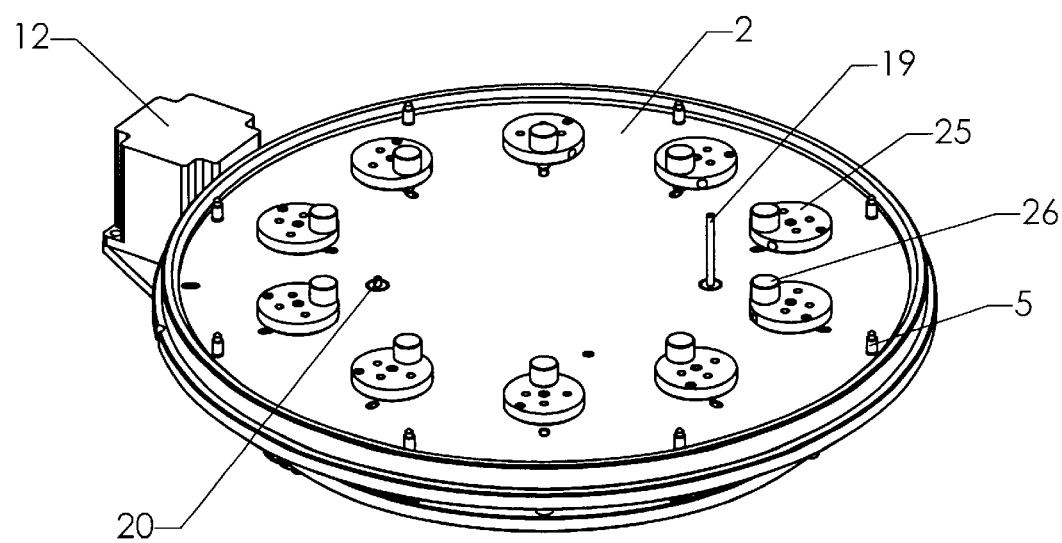
FIG. 9 is a perspective view of the lid embodiment of FIG. 8.

FIGS. 8 and 9 show views of the lower surface of lid 2 (planar and perspective views, respectively). In both views, all cam pins 26 on cam plates 25 are in the innermost rotational position, which would be the position of least tension. When lid 2 is attached to tray 1, each pin 26 fits inside the corresponding sliding tensioner 27, as shown previously in FIG. 5.

FIG. 9 also shows media return tube 19 as it would extend downward into the interior of tray 1 for withdrawal of media and maintenance of media at the proper level. (Return tube 19 extends upward in this view, as this is a view of the bottom surface of lid 2.) Entry of media supply tube 20 into the interior space at a higher level than that of return tube 19 (when assembled in the correct orientation) is also apparent from this view.

Figure 10:
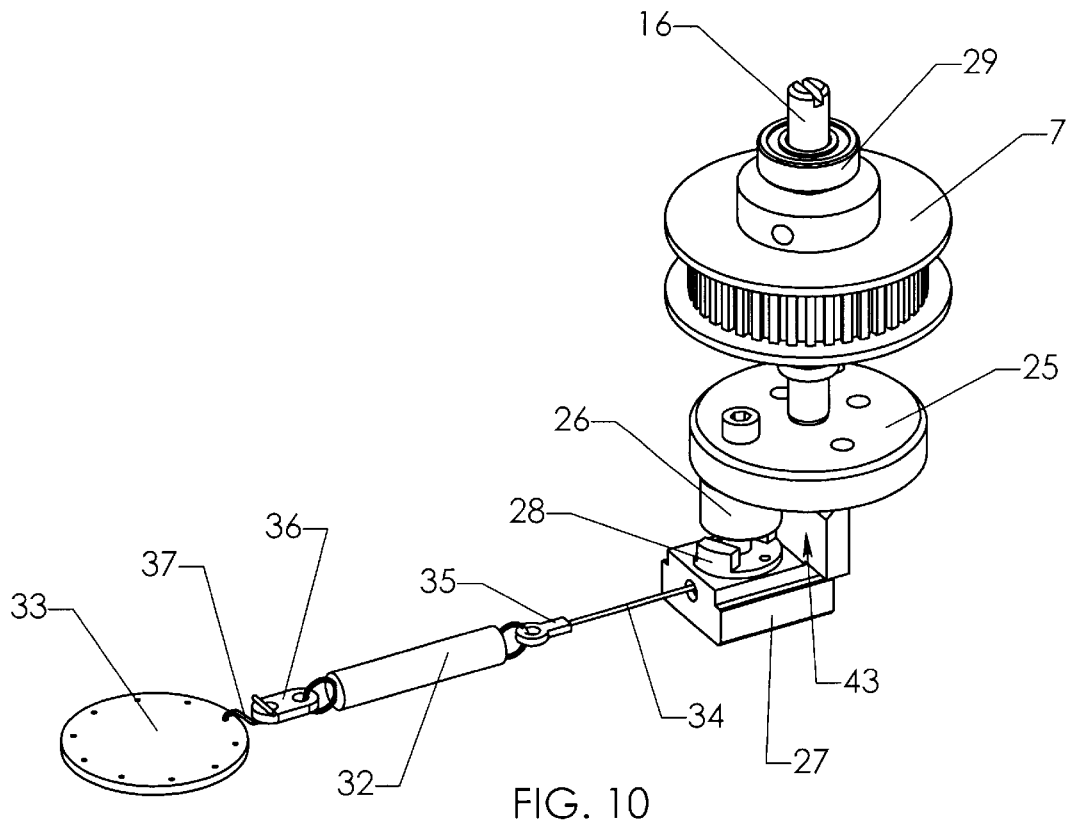
FIG. 10 is a perspective detail view showing connection of a sample tissue to a powered drive belt via a tension spring, sliding tensioner, cam plate and pin, and synchronization pulley of the embodiment of FIG. 1.
Figure 11:
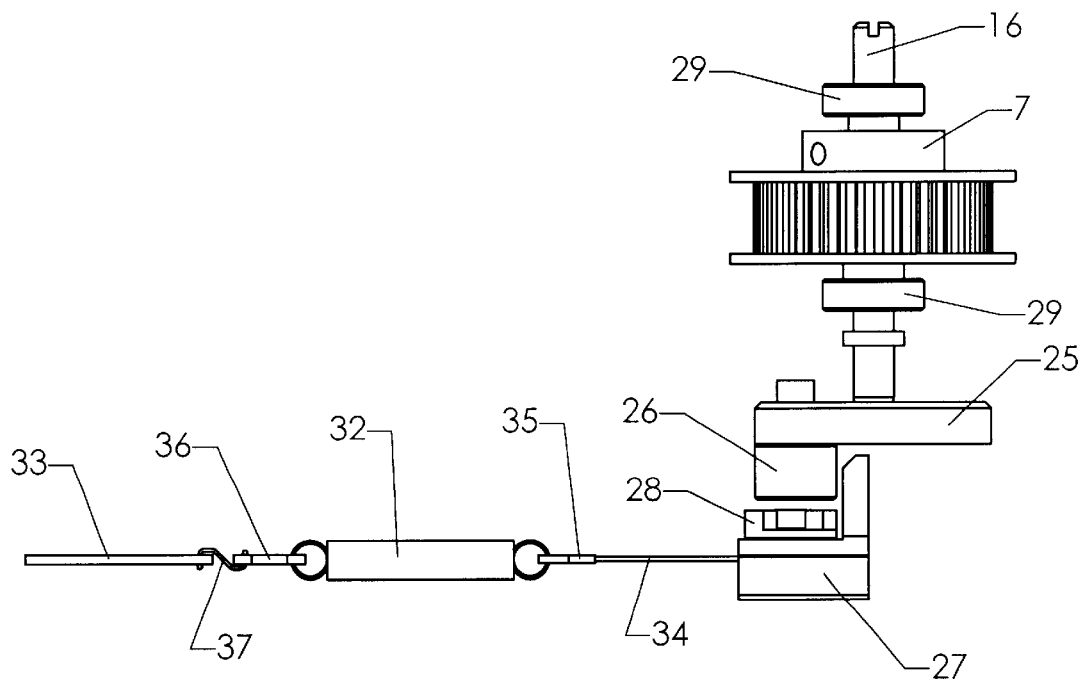
FIG. 11 is a vertical planar view of the detail view shown in FIG. 10.

FIGS. 10 and 11 (perspective and side planar views, respectively) show details of an attachment of sample 33, through various linkage members, to a synchronization pulley 7. Pulley 7, whose shaft 16 is held in position by bearings 29 in the upper and lower bearing plates (not shown) supplies rotational motion to cam plate 25 and cam pin 26. Cam pin 26 slidably engages a contact face 43 of sliding tensioner 27. Sliding tensioner 27 additionally comprises a tension-adjusting pulley 28, which allows adjustment of initial tension on the sample. Cord 34 wraps around tension adjusting pulley 28, so that rotation of pulley 28 can increase or decrease initial tension on the sample, as desired. Once the appropriate initial tension is selected, the pulley is locked in place by a set screw (not shown).

The other end of cord 34 is attached via eye fitting 35 to extension spring 32, which provides a dynamic linkage to the sample (rather than rigid; see previous discussion of the method). A connecting link 36 connects the other end of extension spring 32 to connecting tag 37, which makes the final connection to tissue sample 33.

Figure 12:
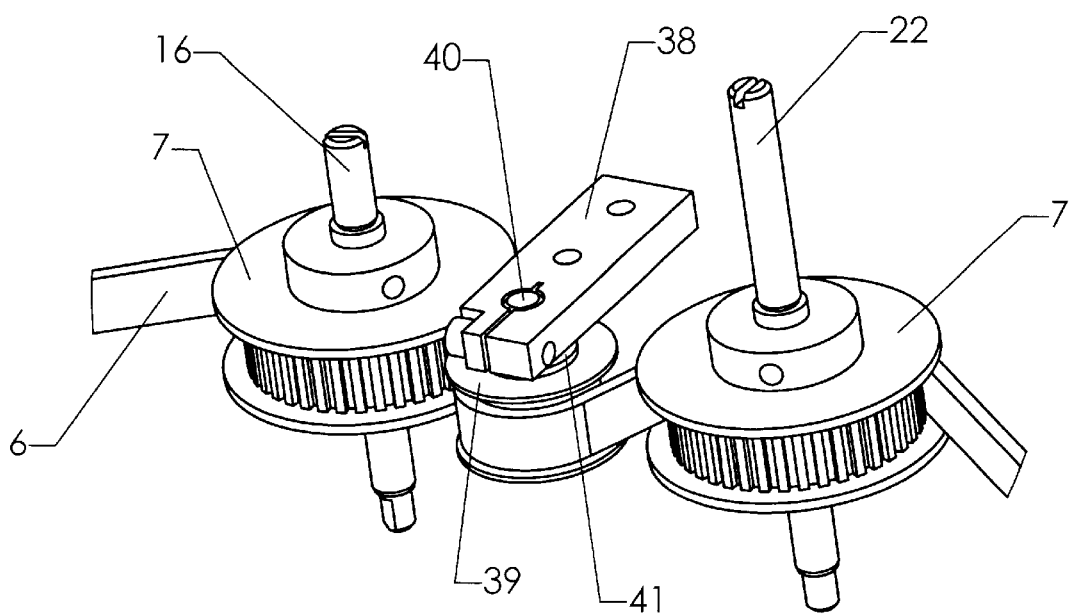
FIG. 12 is a perspective view showing a common drive belt driving multiple synchronization pulleys in the embodiment of FIG. 1.

FIG. 12 shows details of the connection of main drive timing belt 6 in the region of (in this embodiment) attachment to drive motor 12. A normal-length pulley drive shaft 16 is seen in the left portion of the figure, while an extended-length pulley drive shaft 22 (here the one that engages drive pulley 8, not shown) is seen at the right portion of the figure. Timing belt 6 is seen engaging both synchronization pulleys 7 and also engaging idler pulley 39. Idler pulley shaft 40 rotates in idler ball bearing 41 located in idler adjuster 38, which is used to adjust tension of timing belt 6 for proper operation.

Figure 13:
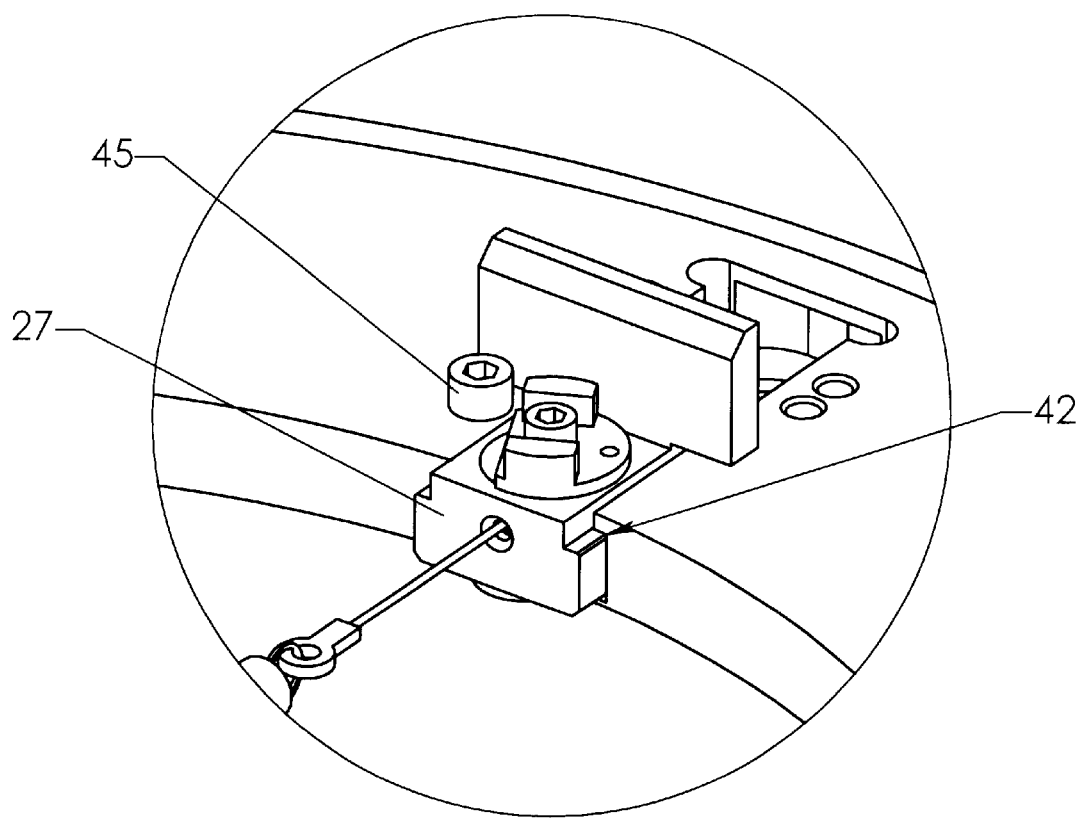
FIG. 13 is a perspective view showing details of a sliding tensioner of the embodiment of FIG. 1.

FIG. 13 is a perspective view of an individual sliding tensioner 27 in its sliding mount 42 prior to attachment of lid 2 (and its components, including cam pin 26, which will engage tensioner 27). As mentioned above, extension spring 32 (not shown) urges tensioner 27 toward the sample (forward) when a sample is present. Excessive forward motion is prevent by setscrew 45 in this embodiment, which prevents tensioner 27 from sliding out of its mount 42. Other embodiments can provide different sliding mount structures, as is well understood in the art.

The invention now being generally described and a specific apparatus described in detail, the same will be better understood by reference to the following examples of the results obtained using an apparatus of the invention, which are provided here for illustration only and are not to be considered limiting of the invention unless so specified.

EXAMPLE

Human full thickness skin was obtained from discarded surgical material following abdominoplasty under informed consent. Immediately upon removal the tissue was placed in 2 liters of sterile transport media, epidermal side up and transported to the laboratory at 4° C. The tissue was defatted using standard aseptic technique, and 6.74 $cm^2$ punches were made using a hardened steel blade. The circular tissue was placed epidermal side up in the expansion device described in the Figures and in the detailed description above and was attached to the device using nylon "T" tags that were inserted through the tissue in a radial pattern of equal spacing. Medium was added, and initial tension was set to 100 g per attachment. The device was sealed and the motor activated to begin force cycling at 10 cycles per minute. The tissue area was measured prior to initiating cycling. Control tissue was placed in an organ culture device in which the tissue sits on a stainless steel grid (under no load) or was set up in an expansion device as described under tension but was not cycled. The tissue was incubated at 37° C. The media was composed of DMEM containing 4.5 g/L glucose and the following additives: L-glutamine, 2 mM; hydrocrtisone, 0.28 $\mu$M; insulin, 4.4 $\mu$M; ascorbic acid, 0.3 mM; penicillin, 105 U/L; streptomycin, 100 mg/L. The device was operated in an air atmosphere with $CO_2$ added for buffering capacity and $O_2$ to prevent hypoxia, as necessary.

After stretching, the skin was measured and removed from the device. The tissue was then prepared for histology, biochemical analysis, and animal transplantation. Tissue appeared to be viable under histological examination and other forms of examination after stretching.

After five days in culture full thickness human skin that had been stretched by applying a cycling load increased 3 fold in surface area. The tissue remained viable with an intact epidermis and dermis. When skin from the same patient was either placed under no load or placed under 100 g/attachment of load but not cycling, there was no significant increase in surface area that could be measured during the same time period. This example illustrates that pulsatile tissue expansion not only allowed rapid tissue expansion, but also allowed tissue expansion to occur at a force less than that necessary to cause expansion in the absence of pulsatile motion.

| | % Increase in Surface Area | | | | | |
|---|---|---|---|---|---|---|
| Day | 0 | 1 | 2 | 3 | 4 | 5 |
| No Load | 0 | 0 | 0 | 0 | — | — |
| Static Load | 0 | 3 | 1 | 0 | 0 | 0 |
| Cyclical Load | 0 | 21 | 53 | 120 | 151 | 203 |

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What we claim is:

1. An in vitro apparatus for increasing the rate of expansion of tissue area and volume, comprising:
    a container having an interior space adapted to contain a cell culture medium,
    sliding mounts located at multiple locations in said interior space,
    sliding tensioners adapted to be attached to a tissue sample and slidably connected to said sliding mounts,
    rotating cams adapted to engage said tensioners and move said tensioners in said sliding mounts when said cams rotate, and
    a control mechanism that rotates said cams in unison,
    whereby rotation of said cams results in radial motion of said sliding tensioners, thereby resulting in increased tension on a sample when said sample is attached to said sliding tensioners and said tensioners are moved away from each other and in reduced tension on said sample when said sliding tensioners are moved toward each other; and
    a controller, operably connected to said control mechanism, wherein said controller causes said device to subject said tissue to stretching forces that alternatively increase and decrease to provide a series of stretch and relax phases during a period of tissue expansion without intervention of an operator.

2. The apparatus of claim 1, wherein said sliding mounts are present in said interior space in pairs located on opposite sides of said interior space and aligned along a single sliding axis.

* * * * *